United States Patent [19]

Chynoweth et al.

[11] Patent Number: 4,735,724
[45] Date of Patent: Apr. 5, 1988

[54] SOLIDS CONCENTRATING ANAEROBIC DIGESTION PROCESS AND APPARATUS

[75] Inventors: David P. Chynoweth, Gainesville, Fla.; Vipul J. Srivastava, Forest Park, Ill.; Richard Biljetina, Skokie, Ill.; Thomas D. Hayes, Schaumburg, Ill.

[73] Assignee: Gas Research Institute, Chicago, Ill.

[21] Appl. No.: 891,651

[22] Filed: Jul. 30, 1986

[51] Int. Cl.$^4$ .............................................. C02F 3/28
[52] U.S. Cl. .................................. 210/603; 210/612; 210/617; 210/180; 210/194; 210/218; 48/197 A; 435/167
[58] Field of Search ............... 210/603, 218, 180, 630, 210/617, 194, 197, 612; 48/197 A, 111; 435/167, 801

[56] References Cited

U.S. PATENT DOCUMENTS

| | | | |
|---|---|---|---|
| 1,806,698 | 5/1931 | Miller | 210/180 |
| 1,838,474 | 12/1931 | Buswell et al. | 48/197 A |
| 1,838,475 | 12/1931 | Buswell | 48/197 A |
| 1,880,773 | 10/1932 | Buswell et al. | 210/603 |
| 4,022,665 | 5/1977 | Ghosh et al. | 210/603 |
| 4,040,953 | 8/1977 | Ort | 210/603 |
| 4,157,958 | 6/1979 | Chow | 210/170 |
| 4,208,279 | 6/1980 | Varani | 210/180 |
| 4,311,593 | 1/1982 | Benjes et al. | 210/610 |
| 4,316,961 | 2/1982 | Klass et al. | 210/603 |
| 4,329,428 | 5/1982 | Ghosh et al. | 210/611 |
| 4,351,729 | 9/1982 | Witt | 210/603 |
| 4,388,186 | 6/1983 | Fujimoto et al. | 210/170 |
| 4,396,402 | 8/1983 | Ghosh | 48/197 A |
| 4,424,064 | 1/1984 | Klass et al. | 210/603 |
| 4,505,819 | 3/1985 | Barnes et al. | 210/603 |

FOREIGN PATENT DOCUMENTS

| | | | |
|---|---|---|---|
| 0044948 | 2/1982 | European Pat. Off. | 435/167 |
| 207696 | 3/1984 | Fed. Rep. of Germany | 210/603 |
| 58-128198 | 7/1983 | Japan | 210/603 |
| 649576 | 5/1985 | Switzerland | 435/167 |

OTHER PUBLICATIONS

Perry L. McCarty, "One Hundred Years of Anaerobic Treatment", Dept. of Civil Engineering, Terman Engineering Center, presented at the Second International Conference on Anaerobic Digestion, Travemude, Germany, 9/7/81.

G. Lettinga, A. Th. Van Der Geest, S. Hobma and J. V. D. Laan, "Anaerobic Treatment of Methanolic Wastes", Water Research, vol. 13, pp. 725 to 737, Pergamon Press Ltd., (1979).

G. Lettinga et al, "Upflow Sludge Blanket Processes", 3rd International Symposium on Anaerobic Digestion, 1983, Cambridge, MA.

G. Lettinga et al, "Anaerobic Treatment of Raw Domestic Sewage at Ambient Temperatures Using a Granular Bed UASB Reactor, Biotechnology and Bioengineering, vol. XXV, pp. 1701-1723, (1983).

Graham F. Andrews, "Fluidized-Bed Fermenters: A Steady-State Analysis, " Biotechnology and Bioengineering, vol. XXIV, pp. 2013-2030, (1982).

Donald L. Klass et al, "Methane Production by Anaerobic Digestion of Bermuda Grass", presented at Symposium on Biomass as a Nonfossil Fuel Source ACS/Chemical Society of Japan Joint Chemical Congress, Honolulu, HI, Apr. 1-6, 1979.

Richard P. Lecuyer, "An Economic Assessment of Fuelgas from Water Hyacinths," and Jerome H. Marten, Symposium Papers, Clean Fuels from Biomass, Sewage, Urban Refuse, Agricultural Wastes, Orlando, Florida, Jan. 27-30, 1976.

*Primary Examiner*—Benoît Castel
*Attorney, Agent, or Firm*—Thomas W. Speckman; Ann W. Speckman

[57] ABSTRACT

A non-mixed vertical tower anaerobic digester and anaerobic digestion process provides passive concentration of biodegradable feed solids and microorganisms in an upper portion of a continuous digester volume and effluent withdrawal from the middle to bottom portion of the digester, resulting in increased solids retention times, reduced hydraulic retention times, and enhanced bioconversion efficiency. In addition, due to passive concentration of solids, the non-mixed anaerobic digester accommodates high solids loadings and provides separation of microbial phases within the continuous digester volume to achieve substantially complete bioconversion of biodegradable feedstock components.

25 Claims, 1 Drawing Sheet

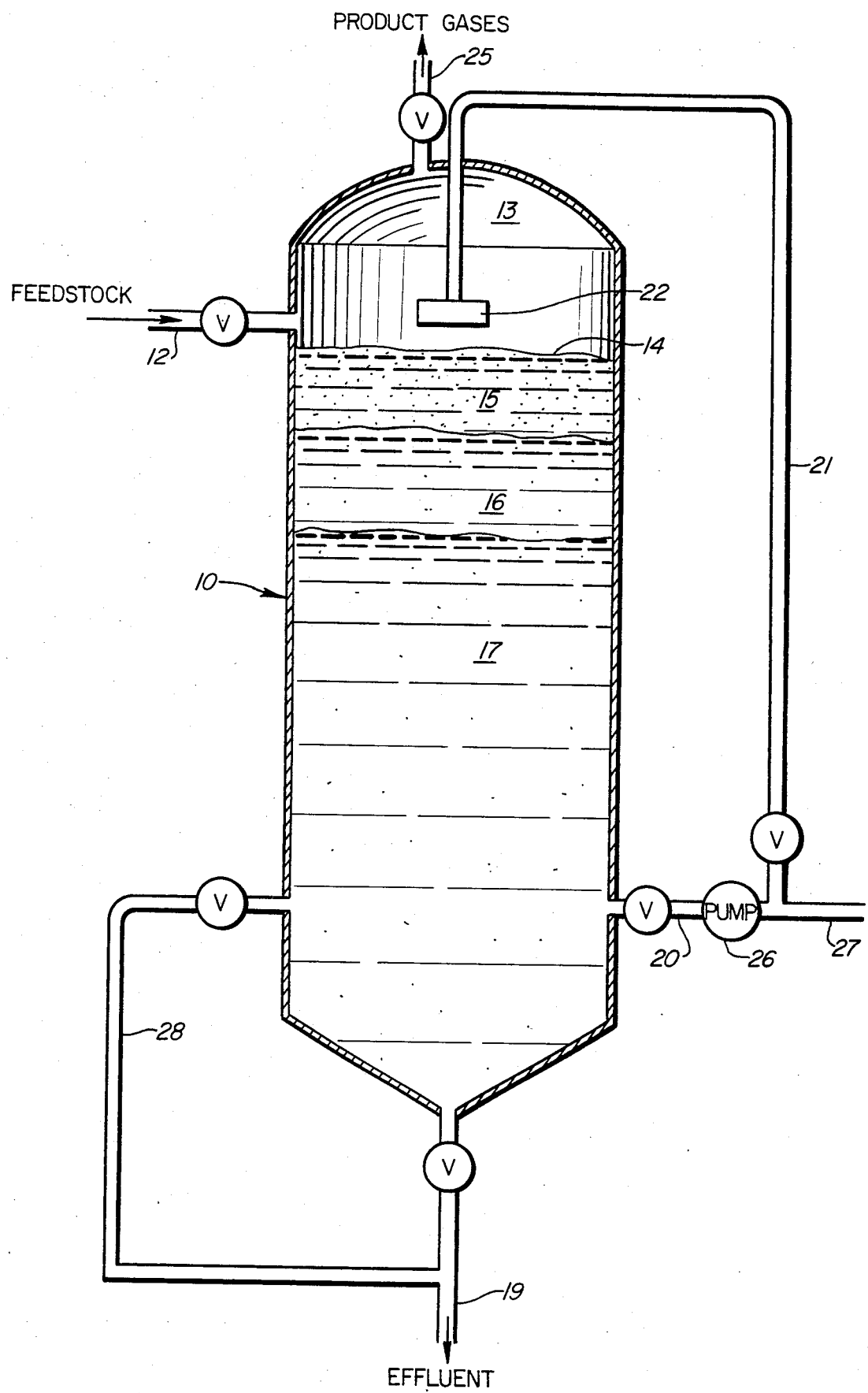

SOLIDS CONCENTRATING ANAEROBIC DIGESTION PROCESS AND APPARATUS

BACKGROUND OF THE INVENTION

1. Field of the Invention

The process and apparatus of the present invention relates generally to bioconversion of biodegradable feedstocks to provide decomposition of organic matter and production of gases such as methane and relates more particularly to anaerobic digestion of particulate containing biodegradable feedstocks in a non-mixed vertical flow reactor wherein solids, including feed and microorganisms are passively concentrated in the upper portion of the digester to provide increased solids and microorganism retention times and reduced hydraulic retention times.

2. Description of the Prior Art

The production of methane and other usable gases by anaerobic digestion of various organic wastes, particularly sewage sludge organic waste, is well known. The organic feed mixture which provides the substrate for anaerobic biodegradation may comprise a wide variety of organic carbon sources, ranging from raw sewage sludge to municipal refuse, or biomass material such as plants and crop wastes. Anaerobic digestion of organic feedstock generally involves hydrolysis fermentation of organic feedstock to acidic intermediates by acid forming bacteria and conversion of the acidic intermediates to useful gases, such as methane, by methane-producing organisms. Many digester designs, feedstock mixtures and additives have been proposed to increase the methane yield from anaerobic digestion and to provide greater conversion efficiency of organic materials to useful products.

Early designs of sewage digesters attempted to biodegrade sewage sludge for the purposes of sludge volume and odor reduction in an unmixed digester, but they were generally unsuccessful because they failed to provide adequate control of solids inventory, and they developed serious problems such as scum buildup, temperature fluctuations, unequal microbial activity and limited contact between the organic material and the bacteria. Most anaerobic digesters installed recently for biological conversion of biomass and community wastes are of the continuously stirred tank reactor design and provide complete mixing of the reactor contents. Solids and hydraulic retention times are equal in continuously stirred tank reactors and both hydrolysis fermentation reactions converting organic materials to acidic intermediates and methane-producing reactions converting acidic intermediates to methane and other gases occur throughout the reactor. These digesters actively discourage the accumulation of floating or settled solids. The history of anaerobic treatment of wastes and digester design, including more recent process developments, is set forth in P. L. McCarty, "One Hundred Years of Anaerobic Treatment", presented at the Second International Conference on Anaerobic Digestion, Travemunde, Germany, Sept. 7, 1981.

Many organic feedstocks have a relatively low suspended solids content, for example less than about 10 percent suspended solids. The high water content of these types of organic feedstocks causes washout of feed solids and microorganisms from continuously stirred tank reactors at high feed loadings due to high dilution rates. Washout of feed solids and microorganisms results in reduced conversion efficiency and unstable digester conditions. Shorter feed solids retention times in the digester, washout of slow growing methanogenic bacteria and accumulation of inhibitory acidic fermentation products contribute to low conversion efficiency and reduced methane production.

An Upflow Anaerobic Sludge Blanket (UASB) process has been developed for bioconversion of feedstocks which contain primarily soluble organic waste wherein small amounts of solids, ordinarily less than 1 percent of the feedstock, and the bacterial mass are allowed to settle in the reactor. The Upflow Anaerobic Sludge Blanket process and reactor are described in the following publications: G. Lettinga, et al, "Anaerobic Treatment of Methanolic Wastes", Water Research, Vol. 33, pp. 725-737, Pergamon Press Ltd. 1979; and G. Lettinga, et al, "Upflow Sludge Blanket Processes", 3rd International Symposium on Anaerobic Digestion, 1983, Cambridge Mass.; and G. Lettinga, et al, "Anaerobic Treatment of Raw Domestic Sewage" at Ambient Temperatures Using a Granular Bed UASB Reactor, Biotechnology and Bioengineering, Vol. XXV, pp 1701-1723, 1983. This reactor design is limited to liquid feedstocks containing less than about 1 percent solids, and it requires effective gas/liquid separators, recycle for bed expansion, and means for distributing the feed over the bottom of the reactor.

Anaerobic filter-type reactors promote the retention of bacteria in the digester by attaching bacteria to fixed inert materials in the digester. Anaerobic filter-type digesters are also limited to primarily liquid feedstocks containing less than about 1 percent solids since they become plugged when solids concentration in the digester increases due to higher solids loading or accumulation of solids over longer periods of operation.

Horizontal plug flow digester designs have been implemented, but horizontal plug flow reactors are limited to use of homogeneous solids feed materials (such as manure), which do not tend to settle by gravity. The horizontal plug flow reactor design encourages rapid disengagement of gas from the liquid phase. Horizontal plug flow reactors generally have poor conversion efficiencies of the biodegradable fraction, on the order of about 40 to 60 percent due to biologically unreactive zones within the digester, shortcircuiting of the feed material, and bacterial washout.

Continuous flow fluidized bed fermenters embodying a tower design or a supported film reactor are described in G. F. Andrews, "Fluidized-Bed Fermenters: A Steady-State Analysis", Biotechnology and Bioengineering, Vol. XXIV, pp 2013-2030, 1982. This article teaches that stratification tends to occur in tower fermenters, and solids concentration varies along the height of the tower fermenter, with a low cell concentration in the upper parts of the tower fermenter leading to a low volumetric productivity.

U.S. Pat. No. 4,208,279 teaches anaerobic digestion of animal waste which is fed to the top and one end of an unstirred digestion volume which is about five times as wide as it is high, and effluent sludge is removed at the opposite end of the reactor. Solids movement in the digester is essentially horizontal and the liquid volume is not agitated, except by gas formation. Suitable solids residence times are one month and over, and the solids feed concentration is about 5 percent.

U.S. Pat. No. 4,311,593 teaches anaerobic digestion of waste water in a digester volume which is about four times as wide as it is high with microorganisms stabilized on high surface area media and providing agitation of the microorganism biomass on the media by gas formation bubbling up through the reactor liquid. U.S. Pat. No. 4,388,186 teaches mechanical condensation of sludge prior to anaerobic digestion of sludge in a vertically elongated, stirred digester tank. The '186 patent also teaches conducting an acid fermentation stage and an acid regression stage separately prior to carrying out an alkaline fermentation stage in the elongated, stirred digester tank. U.S. Pat. No. 1,806,698 teaches a sludge digester wherein solids collect at the bottom, and supernatant liquid accumulating in the upper portion of the digester is recycled to the surface of the digester contents to reduce foam scum. U.S. Pat. No. 1,880,773 also teaches anaerobic digestion of sewage sludge in a digester wherein solids settle to the bottom of the tank and liquid supernatant from the uppe portion of the digester is recirculated to prevent the accumulation of scum or foam at the top surface of the digester contents.

U.S. Pat. No. 4,505,819 teaches top feeding of untreated organic materials in an aqueous medium to a contact reactor, the aqueous bottom contents of which is fed to a fluidized bed anaerobic digester comprising anaerobic bacteria supported on finely divided inert solids. U.S. Pat. No. 4,157,958 teaches anaerobic gasification in a single vessel which is inverted and submerged in a body of water providing both a trap for material in the reactor and also providing liquid agitation to the organic feed material.

Anaerobic digestion of terrestrial plant material to produce methane has been recognized as exemplified by D. L. Klass and S. Ghosh, "Methane Production by Anaerobic Digestion of Bermuda Grass", presented at Symposium on Biomass as a Non-Fossil Fuel Source, ACS/Chem. Soc. of Japan Joint Chemical Congress, Honolulu, Hawaii, Apr. 1–6, 1979. Likewise, the anaerobic digestion of aquatic plant material to produce methane has been recognized as exemplified by R. P. Lecuier and J. H. Marten, "An Economic Assessment of Fuel Gas from Water Hyacinths", Symposium papers, Clean Fuels from Biomass, Sewage, Urban Refuse, Agricultural Wastes, Orlando, Fla., Jan. 27–30, 1976.

U.S. Pat. No. 4,329,428 teaches production of methane gas in higher yields and at higher rates by thermophilic and mesophilic anaerobic digestion of a mixture of plant material of terrestrial or aquatic origin and organic waste. U.S. Pat. No. 4,424,064 teaches production of methane gas with higher yields and at higher rates by thermophilic or mesophilic anaerobic digestion of aquatic plant material, at least a portion or all of which has been grown in organically polluted water. U.S. Pat. No. 4,316,961 teaches higher yields of methane gas at higher rates by thermophilic or mesophilic anaerobic digestion of plant material and/or organic waste of normally low biodegradability in the presence of an extract of different plant material.

Separated two-phase anaerobic digestion processes, wherein in a first acid phase, the microbial population and operating conditions are selected to promote the conversion of organic carbonaceous matter to volatile fatty acids of low molecular weight and in a second methane phase, methanogenic microorganisms convert the volatile fatty acids to product gas composed primarily of methane and carbon dioxide, have been found to enhance conversion efficiency. U.S. Pat. No. 4,022,665 discloses certain specific operating conditions for a two-phase anaerobic digestion process in separated vessels which promotes more efficient conversion of organic material.

SUMMARY OF THE INVENTION

It is an object of the present invention to provide a process and apparatus for anaerobic digestion of feedstocks comprising biodegradable solids wherein passive concentration of solids, including feed and microorganisms, in an upper portion of the digester results in a solids concentration gradient along the vertical length of the digester and provides stable anaerobic digestion reaction conditions.

It is another object of the present invention to provide a non-mixed, vertical flow anaerobic digester wherein biodegradable feedstock is introduced at the top of the reactor and effluent is withdrawn from the middle to the bottom of the reactor to provide increased solids retention times and reduced hydraulic retention times, thereby enhancing bioconversion efficiency.

It is yet another object of the present invention to reduce or eliminate supplemental nutrient requirements and reduce or eliminate scum formation by recycling a small portion of the digester contents withdrawn from the middle to bottom of the digester to the surface of the reactor contents without disturbing the solids concentration gradient established in the digester.

It is still another object of the present invention to provide a process and apparatus for anaerobic digestion of feedstocks comprising biodegradable solids having reduced energy, equipment and maintenance requirements by eliminating costs and energy requirements related to mixing equipment.

It is yet another object of the present invention to provide a non-mixed vertical flow anaerobic digester which can be operated at high solids loadings, which provides passive concentration of solids, including feed solids and microorganisms, which provides separation of microbial phases within the reactor, and which provides uniformly high rates of bioconversion and increased process stability and efficiency.

It is still another object of the process and apparatus of the present invention to provide substantially complete bioconversion of biodegradable components of biomass and organic waste materials in a non-mixed, vertical tower digester to usable product gases, particularly methane.

Feedstock comprising biodegradable solids having a solids concentration of about 1 to about 100 percent is introduced continuously or intermittently at the top of a non-mixed vertical tower digester in a manner which prevents disruption and mixing of the digester contents. When feedstock having a suspended solids concentration in excess of about 10 to about 20 percent is introduced, dilution of the feedstock may be achieved by recirculation to the top of the digester of a portion of the liquid digester contents from the middle to the bottom of the digester, or by introduction of additional liquids to the top of the digester to achieve the desired solids loading level. The non-mixed vertical tower ana robic digester promotes passive concentration of particulate solids, including both biodegradable solids and microorganisms, in the upper portion of the digester.

A solids concentration gradient is established along the height of the digester, with biodegradable solids and microorganisms concentrated toward the top of the reactor due to the low density and fibrous character of the organic solids. Liquids and non-biodegradable components tend to accumulate in the middle and bottom of the digester, and digester effluent is withdrawn from the middle to the bottom of the reactor. Due to the passive concentration of solids in the upper portion of the reactor, biodegradable solids have an increased retention time in the digester, whereas liquids and non-biodegradable components have a reduced retention time, since they migrate to lower portions of the digester and ar withdrawn preferentially. Biodegradable solids retention times in the non-mixed vertical tower-type digester of the present invention are preferably up to ten times longer, and most preferably two to six times longer than hydraulic retention times. Longer biodegradable solids retention times provide increased bioconversion efficiency and increased solids loading capacity.

Passive concentration of biodegradable solids in the digester of the present invention also results in separation of microbial phases within a continuous reactor volume. Due to the unmixed nature of the digester contents and passive solids concentration, hydrolysis fermentation microorganisms ar concentrated near the top of the digester contents. Feed solids introduced at the top of the reactor undergo hydrolysis fermentation in an acid producing zone localized near the top of the reactor, wherein the microbial population comprises various species which convert organic substrate to alcohols and organic acids such as acetic acid, propionic acid and butyric acid. Since different microbial species facilitate each step in the conversion of biodegradable solids to organic acids, the microbial population in the acid producing zone is mixed and conversion to different organic acids and various intermediates occurs simultaneously. The organic acid product of the acid phase digestion remains solubilized in the liquid digester contents while produced gases such as carbon dioxide and methane are released as gaseous products.

Relatively high acidic concentrations resulting from hydrolysis fermentation taking place near the top of the reactor inhibit growth and reproduction of methanogenic microorganisms and methane producing organisms are thus separated from hydrolysis fermentation organisms and are concentrated in a methane producing zone below the acid producing fermentation zone of the digester. Alcohols and organic acids formed in the acid producing zone migrate downward in the digester to the methane producing zone, wherein methanogenic mixed microbial populations facilitate the formation of product gas comprising methane. Product gas bubbles up through the digester contents to the headspace of the digester, providing gentle agitation of the digester contents without disrupting the solids concentration gradient. The hydrolysis fermentation microorganisms and methane producing microorganisms are passively separated in at least two zones in the digester due to the biochemistry of the microorganisms and the anaerobic digestion process.

A portion of the digester effluent removed from the middle to the bottom of the digester may be continuously or intermittently recirculated and distributed on the surface of the digester contents, such as by a fine spray, to provide moisture and nutrients to the concentrated solids at the top of the reactor and/or to provide feedstock dilution without mixing the digester contents or disturbing the concentration gradient of solids in the digester. Recirculation of a portion of the culture volume reduces or prevents the formation of surface scum, promotes conversion of any scum which has formed to useful product gases, and provides necessary moisture and nutrients to solids concentrated near the top of the reactor, reducing or eliminating supplemental inorganic nutrient requirements. Recirculation of liquid culture volume may also reduce or eliminate the need for additives to achieve desired pH adjustment and promote migration of the digester contents along the digester height.

The anaerobic digestion process and apparatus of the present invention accommodates solids loadings from two to five times greater than conventionally used continuously stirred tank digesters, thus providing lower digester volume requirements per pound of solids converted to useful products. Conventional stirred tank reactors operating under mesophilic conditions generally accommodate solids loadings of about 0.05 to about 0.1 lbs. organic matter/ft$^3$/day, and operating under thermophilic conditions generally accommodate about 0.1 to about 0.5 lbs. organic matter/ft$^3$/day. The solids concentrating anaerobic digestion process and apparatus of the present invention preferably operates at solids loadings of about 0.1 to about 0.5 lbs. organic matter/ft$^3$/day under mesophilic conditions, and about 0.2 to about 2.0 lbs. organic matter/ft$^3$/day under thermophilic conditions. Preferred solids loadings for particular applications are highly feed specific.

Passive concentration of solids and the separation of microbial phases within a continuous digester volume according to the present invention results in greater system stability. Any contaminants introduced with the feed remain localized and are less likely to contaminate the entire digester volume, whereas contamination of the entire digester volume occurs rapidly in stirred tank reactors due to continuous mixing. System stability is also enhanced by the separation of microbial phases. Any contaminants which are intfoduced with feed, according to the present invention, are localized in the acid producing zone in the uppr portion of the reactor. The hydrolysis fermentation microbial population is relatively resistant to contaminants and toxic components, while the methane producing microorganisms, in general, have a low resistance to toxic components. In a stirred reactor, toxins are rapidly distributed throughout the digester volume and may destroy a large portion of the methane producing microbial population. In the solids concentrating digester of the present invention, toxins remain localized in the more resistant acid digestion phase. Increased anaerobic digestion system stability results in production of higher quality product gas having a higher methane content, and more efficient utilization of feedstock.

Energy costs related to mechanical mixing equipment and maintenance of mixing equipment are eliminated in the practice of the present invention. Breakdowns of mechanical mixing equipment or breakage of mixing blades generally require shutting down the digester system for repair and require repair under anaerobic conditions to prevent contamination with oxygen. Valves and/or pumps utilized in the practice of the present invention are located externally of the digester contents, and may be conveniently replaced, requiring little or no digester downtime. Costs and energy requirements related to transfer of solids, liquid and gases between separated digesters and maintenance of separated digesters for optimizing different microbial populations and different digestion phase conditions are also eliminated. The present invention provides substantially complete bioconversion of biodegradable components of feedstocks at enhanced bioconversion rates and efficiencies.

BRIEF DESCRIPTION OF THE DRAWING

Further features of the invention will be apparent from the following more detailed description taken in conjunction with the drawing which shows a highly schematic sectional view of a non-mixed vertical tower digester according to one embodiment of the present invention.

DESCRIPTION OF PREFERRED EMBODIMENTS

The term "biomass" as used in this description and the appended claims, includes why of the organisms of the Kingdom Plantae which typically have cell walls composed of cellulose in large part and have nutritive systems in which carbohydrates are formed photosynthetically. The plant material useful in this invention is fresh harvested or stored plant material, and is typically untreated chemically or physically, except for size reduction. Both terrestrial and aquatic plants are suitable. Terrestrial plants include warm season grasses, such as Bermuda Grass and Elephant Grass; cool season grasses, such as Kentucky Blue Grass and Marion Blue Grass; reedy plants such as bamboo, rice, cattails; herbaceous plants as Kudzu and Maze; deciduous trees, such as Eucalyptus and Poplar; and coniferous trees such as white and red pines. Exemplary aquatic plants include water hyacinth, duckweed, algae, sea kelp and sargassum.

The term "organic waste" as used in this disclosure and the appended claims includes all types of organic refuse, including sewage sludge, animal waste, municipal waste, industrial waste, forestry waste, agricultural waste, and the like. By "forestry and agricultural waste" we mean to include portions of plants after some physical or chemical pretreatment, such as stump logging, sawdust, wood chips, cornstalks, corncob and bagasse. Treatment of municipal solid waste and industrial solid waste for removal of desired material such as glass, metals, plastics, stones, and the like, is well known to the art.

Feed material such as biomass, organic waste and forestry and agricultural waste may be digested separately according to the process of the present invention, or mixtures of the waste materials and/or biomass may be utilized as is known to the art. Mechanical degradation of the feed material may be required to achieve the wide range of particle sizes suitable for use in anaerobic digestion according to this invention. Such mechanical degradation is well known to the art. Various pretreatment of the feed material may advantageously be used with the present invention, such as acid or alkaline hydrolysis, but none is required.

Any active producing mesophilic or thermophilic microbial anaerobic digestion system may be used. Anaerobic systems utilizing acid forming bacteria and methane producing organisms as well known in the production of methane from sewage sludge may be employed in the practice of the present invention. A review of the microbiology of anaerobic digestion is set forth in Anaerobic Digestion, 1. The Microbiology of Anaerobic Digestion, D. F. Toerien and W. H. J. Hattingh, Water Research, Vol. 3, pages 385–416, Pergamon Press (1969). As set forth in that review, the principal suitable non-methanogenic bacteria include species from genera including Aerobacter, Aeromonas, Alcaligenes, Bacillus, Bacteroides, Clostridium Escherichia, Klebsiella, Leptospria, Micrococcus, Neisseria, Paracolobactrum, Proteus, Pseudomonas, Rhodopseudomonas, Sarcina, Serratia, Streptococcus and Streptomyces. Exemplary methane-producing organisms suitable for use in the present invention include member of Methanobacterium, Methanococcus and Methanosarcina, specific members being *Methanobacterium formicicum, Methanosarcina barkerii, Methanobacterium omelianskii, Methanococcus vannielii, Methanobacterium sohngenii, Melhanosarcina methanica, Methanococcus mazei, Methanobacterium suboxydans* and *Methanobacterium propionicum*. It is preferred to use mixed cultures to obtain the most complete fermentation action. Nutritional balance and pH adjustments may be made to the digester system as necessary as is known to the art to optimize methane production from the culture used.

As shown in the FIGURE, feedstock comprising biomass, organic waste, forestry and agricultural waste, and mixtures thereof, is conveyed through valved feedstock inlet 12 for introduction near the top of anaerobic digester vessel 10. Feedstock comprising about 1 to about 100 percent solids is continuously or intermittently introduced int anaerobic digester vessel 10 to provide a relatively constant digester contents volume within digester vessel 10. Solids loadings of about 0.1 to about 0.5 lbs. organic matter/ft$^3$/day, and preferably about 0.2 to about 0.3 lbs. organic matter/ft$^3$/day, are suitable for digester operation under mesophilic conditions. Solids loadings of about 0.2 to about 2.0 lbs. organic matter/ft$^3$/day, and preferably about 0.5 to about 1.0 lbs. organic matter/ft$^3$/day are suitable for digester operation under thermophilic conditions. Addition of liquid diluent may be necessary to achieve the desired solids loadings, particularly when feedstock suspended solid concentration exceeds about 10 to about 20 percent. Liquid diluent may be provided to the upper portion of digester 10 to achieve the desired solids loading by recirculation of liquid culture volume from the middle to lower portions of the digester through valved conduit 20, and/or by liquid circulation from external sources through conduit 27.

The anaerobic digester of the present invention comprises non-mixed vertical tower-type reactor 10 having a relatively large height to diameter ratio of about 1:1 to about 6:1, and preferably about 2:1 to about 3:1. Digester vessel 10 may be generally cylindrical, rectangular, or the like, as long as it embodies suitable height to diameter ratios. Similarly, the base and the top of digester vessel 10 may be flat, rounded, cone-shaped, or any other geometry which is convenient or required for a particular application. Suitable height to diameter ratios may be achieved by vertically partitioning conventional digester tanks having a relatively large diameter to height ratio to provide a plurality of separated digester volumes. In a preferred embodiment, impermeable vertical partitions extend to and seal with the base of the digester to provide separated digester culture volumes, but do not extend to the top of the digester vessel, so that a common headspace is provided for product gas withdrawal from all vertically partitioned digester volumes. According to this embodiment a feed manifold may be provided for feed introduction to each digester volume, and no intermixing of solid or liquid digester contents takes place. At least one effluent manifold may likewise be provided for removal and/or recirculation of digester contents from the middle and/or lower portions of the digester vessels.

Non-mixed anaerobic digester vessel 10 promotes passive concentration of particulate solids, including both feed solids and microorganisms in the upper portion of the digester, and promotes separation of two or more microbial phases into at least two zones, such as acid producing zone 15 and methane producing zone 16, within a single continuous digester volume. A solids concentration gradient is established along the height of the digester with biodegradable feed solids and microorganisms concentrated toward the top of the reactor, particularly in acid producing zone 15, and non-biodegradable components and liquids accumulating in the middle and lower portions of the digester, in low solids content zone 17. Digester effluent comprising liquid and non-biodegradable components may be withdrawn through valved effluent withdrawal conduit 19 for disposal or further utilization. Digester effluent may alternatively or additionally be withdrawn through valved effluent withdrawal conduits 20 and/or 28 provided in the lower portion of anaerobic digester 10. Effluent withdrawal conduits 20 and 28 may be provided at any point from about the middle to the bottom of digester vessel 10 to provide withdrawal of digester effluent from low solids content zone 17. Gravity discharge is generally preferred, but a pump may be provided in at least one of the effluent withdrawal conduits to facilitate effluent withdrawal and recirculation.

Digester effluent is continuously or intermittently withdrawn from low solids content zone 17 to provide a relatively constant digester contents volume and to provide suitable solids and hydraulic retention times within digester vessel 10. Due to the passive concentration of solids including feedstock and bacteria in the upper portion of digester vessel 10 and withdrawal of effluent from the middle to bottom portion of digester vessel 10, solids retention time in digester vessel 10 is greater than the hydraulic retention time, preferably about 1.5 to 10 times greater, and most preferably about two to six times greater. Suitable solids and hydraulic retention times for specific applications depend, of course, upon the type of feedstock being digested. In general, solids retention times of about 14 to about 70 days are suitable. Longer solids retention time as compared with hydraulic retention time provides high rates of bioconversion at high solids-loadings and reduces washout of solids, particularly bacteria, from the digester vessel.

A portion of the digester effluent withdrawn from digester vessel 10 through effluent withdrawal conduit 20 may be diverted by the use of pump 26, such as a progressive cavity pump, through effluent recycle conduit 21 and distributed continuously or intermittently on the top of the digester contents through effluent recycle dispersal means 22 to provide moisture and nutrients to the digester contents surface 14, and/or to provide a desired diluent. Effluent recycle dispersal means 22 may comprise one or more spray means, such as the vertical spray nozzle, which distributes effluent over the entire area of digester contents surface 14. Effluent distributed through effluent recycle dispersal means 22 is distributed on surface 14 in a manner which does not disrupt the solids concentration gradient in digester vessel 10. The flow of effluent recycle preferred for specific applications is highly feed specific but, in general, effluent recycle of about 0.5 to about 3.0 gal/gal digester contents/day is preferred, and about 1.0 to about 2.0 gal/gal digester contents/day is especially preferred.

Passive concentration of solids in the upper portion of digester vessel 10 produces a separation of multiple microbial phases, as indicated by acid producing zone 15 and methane producing zone 16, whereby acid forming bacteria and acid producing intermediates are concentrated within acid producing zone 15 and methane producing bacteria and methanogenic intermediates are concentrated within methane producing zone 16. Because the digester contents are non-mixed, localization of an acid producing zone and a methane producing zone occurs naturally, and optimization of reaction conditions in each zone is promoted for the particular feedstock, loading rate, bacterial culture, etc. For example, in addition to spatial separation of the acid producing and methane producing bacteria, the digester contents pH within acid producing zone 15 is naturally lower than the digester contents pH in methane producing zone 16.

Product gases formed in methane producing zone 16 migrate to digester headspace 13 and provide natural flocculation and gentle agitation of the digester culture volume in acid producing zone 15. Because the process and apparatus of the present invention achieve high bioconversion efficiencies of about 90 percent and greater, approximately 20 to 25 percent more methane product gas is produced per unit feedstock according to this invention,-compared to conventional stirred tank digesters. Product gases in digester headspace 13 are withdrawn from digester vessel 10 through product gas withdrawal conduit 25.

The following example sets forth specific feedstocks, digester operating conditions, and the like for the purpose of more fully understanding preferred embodiments of the present invention and is not intended to limit the invention in any way.

EXAMPLE

Feedstock comprising a mixture of water hyacinth and primary sludge was anaerobically digested according to the process of the present invention in a non-mixed vertical tower digester. Water hyacinth was ground to achieve average feedstock sizes of about 0.12 inch. The blend ratio of water hyacinth:primary sludge was about 0.8:1 to provide a mixed feedstock having an average solids content of about 3.76 wt. percent; an average volatile solids (VS) concentration of about 85.5 wt. percent TS; an average volatile acids content of 3400 mg/L as acetic acid; a pH of about 5.18; and an average alkalinity of 3400 mg/L $CaCO_3$.

The digester was operated under steady state conditions for a period of four weeks. Blended feedstock was introduced once daily at the top of the digester, effluent was withdrawn from the bottom, and product gas was withdrawn from the digester headspace. The average daily loading rate was about 0.19 lb. volatile solids (VS)/ft$^3$ to a culture volume of 137 ft$^3$. Anaerobic digestion was carried out under mesophilic conditions at an average temperature of about 94.4° F. The pH of the digester contents ranged from about 7.1 to about 7.9, with localized zones within the reactor having higher or lower pH values within this range. No additives were required for pH adjustment or nutrient supplement. The volatile acids content ranged from about 50 to about 2300 mg/L as acetic acid, with localized zones within the reactor having higher or lower volatile acids contents. Approximately one volume of digester culture was recirculated from the lower portion of the culture volume by a progressive cavity pump and distributed as a fine spray over the upper surface of the culture volume during a four hour period each day, providing moisture and nutrients to the feedstock solids. The recirculated liquid had 1.91 wt. percent average solids content; 75.1 wt. percent average Volatile Solids concentration; 1100 mg/L Volatile Acids Content as acetic acid; pH 7.2; and average alkalinity of 5200 mg/L as $CaCO_3$. The carbon balances performed around the reactor during the test periods indicated that the average hydraulic retention time was 11 days, while the average solids retention time was 35 days.

The average daily gas production was 320 SCF with total product gas yield of the anaerobic digestion syste of 12.4 SCF/lb volatile solids (VS) added. The methane content of the product gas was about 64 volume percent, providing a methane yield of about 7.9 SCF/lb VS added and about 7.2 SCF/lb organic matter added. The above anaerobic digestion according to the process and apparatus of the present invention resulted in greater than 90 percent conversion of the maximum biodegradable yield. The methane production rate was 1.5 vol/-vol.-culture-day; Volatile Solids Reduction 69 wt. percent; carbon conversion 62 wt. percent; and carbon balance 105 wt. percent. The energy requirement reduction using a pump for recirculation versus continuous mixing with a conventional paddle impeller was about 90 percent.

While in the foregoing specification this invention has been described in relation to certain preferred embodiments thereof, and many details have been set forth for purpose of illustration, it will be apparent to those skilled in the art that the invention is susceptible to additional embodiments and that certain of the details described herein can be varied considerably without departing from the basic principles of the invention.

We claim:

1. A process for anaerobic digestion of biodegradable feedstock comprising:
   introducing feedstock comprising biodegradable solids and non-biodegradable components into an upper portion of a non-mixed vertical tower digester having an active producing microbial anaerobic digestion population comprising hydrolyss fermentation organisms and methanogenic organisms suspended in liquids;
   passively concentrating said biodegradable solids and said microorganisms in an upper zone of said vertical tower digester and passively concentrating said liquids and said non-biodegradable components in a middle zone and a lower zone of said vertical tower digester;
   passively concentrating said hydrolysis fermentation organisms in an upper portion of said upper; zone and passively concentrating said methanoganic organisms in a lower portion of said upper zone of said vertical tower digester;
   biodegrading said biodegradable solids by said active producing microbial anaerobic digestion population in said upper zone of said vertical tower digester producing product gases and organic liquids;
   retaining said biodegradable solids in said upper zone for a solids retention time and retaining said liquids in said middle and lower zones for a hydraulic retention time less than said solids retention time;
   withdrawing an effluent comprising said liquids and said non-biodegradable components from at least one of said middle and lower zones of said vertical tower digester; and
   withdrawing said product gases from a headspace of said vertical tower digester.

2. A process according to claim 1 wherein said non-mixed vertical tower digester has a height to diameter ratio of about 1:1 to about 6:1.

3. A process according to claim 2 wherein said non-mixed vertical tower digester has a height to diameter ratio of about 2:1 to about 3:1.

4. A process according to claim 1 wherein biodegrading said biodegradable solids in said upper zone of sid vertical tower digester further comprises converting said biodegradable solids to alcohols, organic acids and product gases in an acid producing zone in said upper portion of said upper zone of said vertical tower digester and converting said alcohols and organic acids to product gases in a methane producing zone below said acid producing zone in said lower portion of said upper zone of said vertical tower digester.

5. A process according to claim 4 wherein said product gases produced in said acid producing zone and said methane-producing zone migrate to said headspace of said vertical tower digester, thereby promoting said passive concentration of said biodegradable solids and said mircoorganisms in said upper zone of said digester.

6. A process according to claim 1 wherein said solids retention times are about 1.5 to 10 times greater than said hydraulic retention times.

7. A process according to claim 6 wherein said solids retention times are about two to six times greater than said hydraulic retention times.

8. A process according to claim 1 additionally comprising recirculating a portion of said effluent from at least one of said middle and lower zones of said digester and distributing said recirculated effluent on an upper surface of said upper portion of said digester, thereby providing moisture and nutrients to said upper zone comprising passively concentrated biodegradable solids and microorganisms.

9. A process according to claim 8 comprising recirculating said effluent to said upper surface of said upper portion of said digester at a rate of about 0.5 to 3.0 gal./gal. digester contents/day.

10. A process according to claim 9 comprising recirculating said effluent to said upper surface of said upper portion of said digester at a rate of about 1.0 to about 2.0 gal./gal. digester contents/day.

11. A process according to claim 1 wherein said active producing microbial anaerobic digestion population comprises a mesophilic microbial population and said non-mixed vertical tower digester is maintained under mesophilic conditions.

12. A process according to claim 11 wherein solids loadings of about 0.1 to about 0.5 lbs. organic matter/ft$^3$/day are maintained in said non-mixed vertical tower digester.

13. A process according to claim 12 wherein solids loadings of about 0.2 to about 0.3 lbs. organic matter/ft$^3$/day are maintained in said non-mixed vertical tower digester.

14. A process according to claim 1 wherein said active producing microbial anaerobic digestion population comprises a thermophilic microbial population and said non-mixed vertical tower digester is maintained under thermophilic conditions.

15. A process according to claim 14 wherein solids loadings of about 0.2 to about 2.0 lbs. organic matter/ft$^3$/day are maintained in said non-mixed vertical tower digester.

16. A process according to claim 15 wherein solids loadings of about 0.5 to about 1.0 lbs. organic matter/ft$^3$/day are maintained in said non-mixed vertical tower digester.

17. A process according to claim 1 additionally comprising introducing a liquid diluent into said upper portion of said non-mixed vertical tower digester.

18. A process according to claim 17 wherein said liquid diluent is provided by recirculating said liquids from at least one of said middle and lower zones of said vertical tower digester.

19. A process according to claim 1 wherein said biodegradable feedstock is selected from the group consisting of: biomass, organic waste, forestry and agricultural waste, and mixtures thereof.

20. A process according to claim 1 wherein said effluent is withdrawn from said non-mixed vertical tower digester by gravity discharge.

21. A process according to claim 1 wherein said effluent is withdrawn from said non-mixed vertical tower digester by means of at least one pump.

22. A process according to claim 1 wherein greater than about 90 percent of said biodegradable solids are biodegraded.

23. A process according to claim 8, wherein said effluent is continuously recirculated and distributed of said upper surface of said upper portion said digester.

24. A process according to claim 1, wherein said feedstock is introduced at least once daily into said upper portion of said non-mixed vertical tower digester.

25. A system for anaerobic digestion of biodegradable feedstock comprising:

a non-mixed vertical tower digester having a height at least as great as its diameter and a continuous internal space, a feedstock inlet means in an upper portion of said digester, at least one effluent withdrawal means in a lower portion of said digester, and a product gas withdrawal means in a headspace of said reactor;

an active producing microbial anaerobic digestion population comprising hydrolysis fermentation organisms and methanogenic organisms concentrated in an upper zone of said digester continuous internal space with said hydrolysis fermentation organisms passively concentrated in an upper portion of said upper zone and said methanogenic organisms passively concentrated in a lower portion of said upper zone, said microbial anaerobic digestion population converting biodegradable solids comprising said feedstock to product gases and organic liquids;

digester effluent comprising liquids and non-biodegradable components concentrated in a middle zone and a lower zone of said digester.

* * * * *